United States Patent [19]

Crickard et al.

[11] 4,192,177

[45] Mar. 11, 1980

[54] APPARATUS AND METHOD FOR PRESSURE TESTING OF TUBULAR BODIES

[75] Inventors: James L. Crickard, Huntington, W. Va.; Harold L. Sheets, Chesapeake, Ohio

[73] Assignee: Huntington Alloys, Inc., Huntington, W. Va.

[21] Appl. No.: 867,820

[22] Filed: Jan. 9, 1978

[51] Int. Cl.² ............................................. G01M 3/28
[52] U.S. Cl. ...................................... 73/49.5; 73/49.1; 138/90
[58] Field of Search ...................... 73/49.5, 49.6, 49.1, 73/40, 37, 49.4; 138/90; 277/3, 27

[56] References Cited

U.S. PATENT DOCUMENTS

| 521,835 | 6/1894 | Tillinghast | 138/90 |
| 1,466,450 | 8/1923 | Kothe | 73/49.5 X |
| 1,637,956 | 8/1927 | Moriarty | 73/49.5 |
| 1,861,684 | 6/1932 | Dague | 73/49.5 X |
| 1,973,674 | 9/1934 | Rosenkranz | 73/49.6 |
| 2,534,830 | 12/1950 | Philo | 138/90 X |
| 2,997,070 | 8/1961 | Penhale | 138/90 |
| 3,334,906 | 8/1967 | Arnold | 277/3 |
| 4,086,806 | 5/1978 | Covey et al. | 73/49.5 |

FOREIGN PATENT DOCUMENTS

| 488116 | 1/1976 | U.S.S.R. | 73/49.5 |
| 491870 | 3/1976 | U.S.S.R. | 73/49.5 |

*Primary Examiner*—Gerald Goldberg
*Assistant Examiner*—Joseph W. Roskos
*Attorney, Agent, or Firm*—E. C. MacQueen

[57] ABSTRACT

Method and apparatus for fluid pressure testing of tubes or pipes is provided wherein the tube or pipe under test is sealed at the ends by a resilient O-ring between the inside diameter of the tube or pipe and convex, preferably conical faces at each end of the tube or pipe, with the conical faces being held firmly in place against the outward thrust of the test fluid pressure by hydraulic action utilizing the pressurized testing fluid.

10 Claims, 10 Drawing Figures

APPARATUS AND METHOD FOR PRESSURE TESTING OF TUBULAR BODIES

The present invention is directed to an apparatus and method for hydraulic testing of hollow cylindrical bodies such as tubes and pipes.

In the manufacture of tubular bodies such as tubes and pipes, it is necessary that the hollow cylindrical body be subjected to hydrostatic testing in order to eliminate parts which are flawed, for example, tubes which are porous or spilt or otherwise defective. It is desirable that the method chosen for hydraulic testing be readily repeatable, that it be applicable to tubes or pipes of varying diameter and lengths, that it be quick, reliable, inexpensive and capable of being performed by inexperienced personnel. Generally speaking, hydraulic testing of tubing or pipe requires that the ends of the part to be tested be sealed in a manner such that fluid pressure can be introduced, maintained and relieved from the tube under test. A number of expedients have been adopted to accomplish this objective, all of which as far as is known to the inventors are accompanied by limitations and drawbacks which indicate that improvement in the testing technique is desirable and necessary. Thus, the following methods have been employed:

(1) the ends of the tube to be tested have been sealed with metal plugs fitting closely into the tube inside diameter and having a resilient sealing element. Different plugs must be provided for each internal diameter of tube to be tested. Such plugs must be held in place by expanded serrated jaws which grip the inside of the tube or which are restrained externally from being pushed outward from the tube by the hydraulic pressure employed in the course of the test. Tie rods and other means have been accomplished for this purpose.

(2) Pressure heads have been employed which allow the insertion of the tube and provide an effective seal on the outside surface of the tube shell. When this method is employed the pressure heads must be restrained from being pushed away from the end of the tube under the hydraulic testing pressure either by gripping the outside of the tube surface, by tie rods, or by other means. Again, separate tooling must be provided for each tube diameter to be tested.

(3) The tube ends have been welded shut by plates or other metal elements which are provided with a passage to introduce the fluid under pressure to the interior of the tube. These plates must be cut off after the test. The technique is expensive in that welding must be employed and wastage of material results when the welded tube ends are cut off subsequent to the test.

(4) Another method involves placing metal plates on the ends of the tube to be tested with a resilient sealing element between the tube end and the plate. At least one of the plates must have a passage for introduction of the testing pressurized fluid and both plates must be restrained to prevent any movement away from the tube ends caused by the hydraulic pressure within the tube during the course of the test. This technique has been limited to the use of relatively low pressures due to yielding or stretching of the metal in the sealing system due to forces caused by the internal hydraulic pressure during test and which tends to force open the sealing elements.

All of the foregoing testing expedients have particular defects and disadvantages in practice. Thus, methods (1) and (2) set forth hereinbefore require that expensive metal tooling be provided for each size of tubing to be tested which tooling fits closely with a tolerance within a few thousandths of an inch to either the inside or outside surface of the tube shell under test so as to effectively support and prevent blow-out of the resilient seal employed to contain the fluid pressure. The use of tie rods to prevent blow-out of the sealing means according to these methods is expensive, labor-intensive and can cause crushing or buckling of the tube or pipe under test due to excessive column-type loading. As previously noted, method (3) is not practical in use due to costs. Method (4) mentioned hereinbefore does not work well in practice and is effective at only relatively low test pressures.

In the light of the foregoing discussion of prior art testing methods, it is clear that improvements are needed in this necessary and required operation involving the hydraulic pressure testing of tubes or pipes.

THE INVENTION

The present invention provides a quick, effective and inexpensive method for reliably subjecting tubular bodies to hydraulic testing. Apparatus employed in accordance with the invention is illustrated in the accompanying drawing wherein:

FIG. 8 is a section at the junction of the end wall of a tubular body to be tested and the headstock face showing the location of the resilient O-ring prior to test;

FIG. 9 is a similar section to that of FIG. 8 during the course of the test depicting compression of the resilient O-ring seal between the end wall of the tubular body and the headstock face under the pressure of the pressure test fluid within the tubular body.

Generally, the invention relates to apparatus and method for fluid pressure testing of tubular bodies having a range of diameters. The apparatus comprises a headstock and a tailstock having a common axis with said headstock and said tailstock having convex faces projecting toward each other and with said convex faces being adapted in combination to hold a tubular body therebetween and to form a pressure tight seal at the ends thereof by means of resilient O-rings within said tubular body at the junctions of said convex faces and the ends of said tubular body, with the headstock comprising telescoping rearward and forward elements and with the rearward element being fixably mounted and with the forward element bearing said headstock convex face, said headstock convex face having at least one sensing hole communicating through said forward telescoping element to the junction between the telescoping elements whereby fluid pressure communicated from said sensing hole to the junction between the rearward and forward elements of the headstock acts hydraulically to move said forward telescoping element away from said rearward telescoping element and against the end of the tubular element undergoing test. Advantageously the projecting faces on the headstock and the tailstock are conical since generally the tubular body being tested will be round in section. Furthermore, the configuration of the junction between the rearward and forward elements of the headstock are designed to constitute one or more hydraulic cylinders having an effective area presented to the hydraulic fluid substantially greater than the area of the inside diameter of the tubular element undergoing test so as to insure firm closure and sealing of the testing fluid within the tube being pressure tested.

Figure 1:
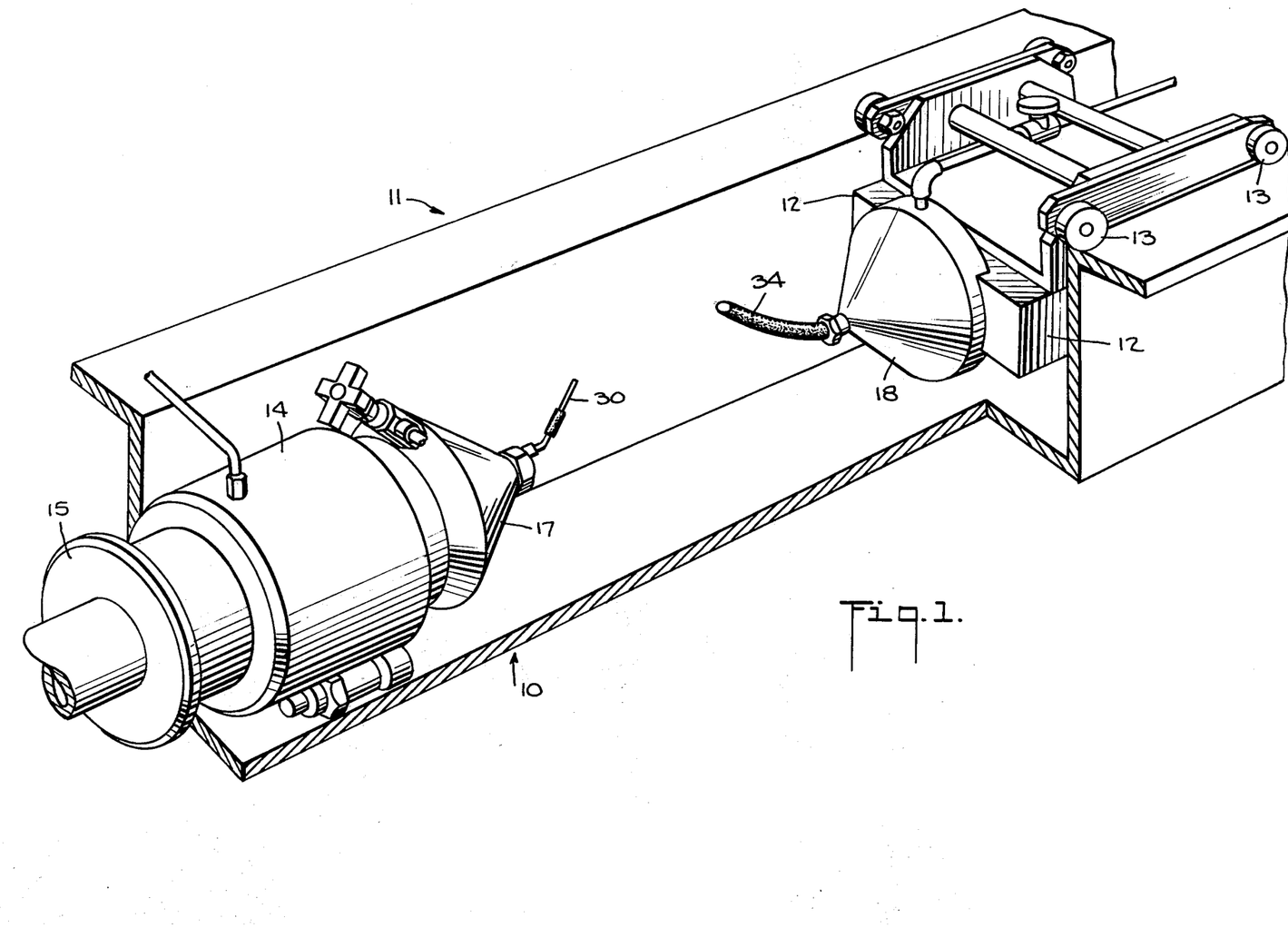
FIG. 1 is a perspective view, partially in section, depicting apparatus in accordance with the invention.
Figures 2, 3, 4, 5:
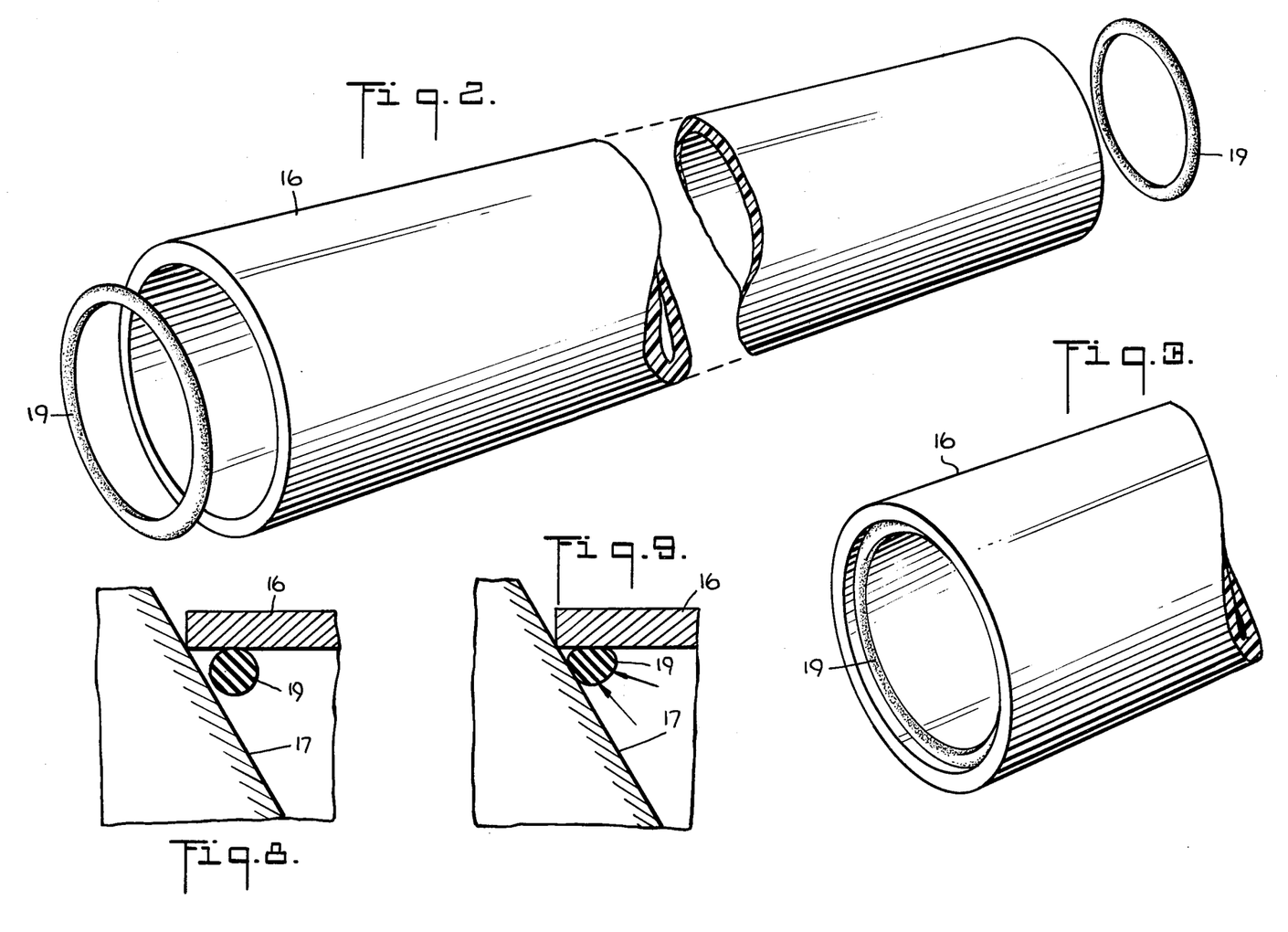
FIG. 2 is a perspective view of a tubular body to be tested in accordance with the invention depicting the O-ring seals prior to insertion thereof into the ends of the tubular body.
FIG. 3 is a perspective view of an end of a tubular body to be tested in accordance with the invention depicting a resilient O-ring seal in place prior to pressure testing.
FIG. 4 depicts in vertical section apparatus in accordance with the invention with a tubular body in place therein prior to insertion of the pressure testing fluid.
FIG. 5 depicts in vertical section apparatus in accordance with the invention with a tubular body in place therein during the course of a pressure test.
Figure 4:
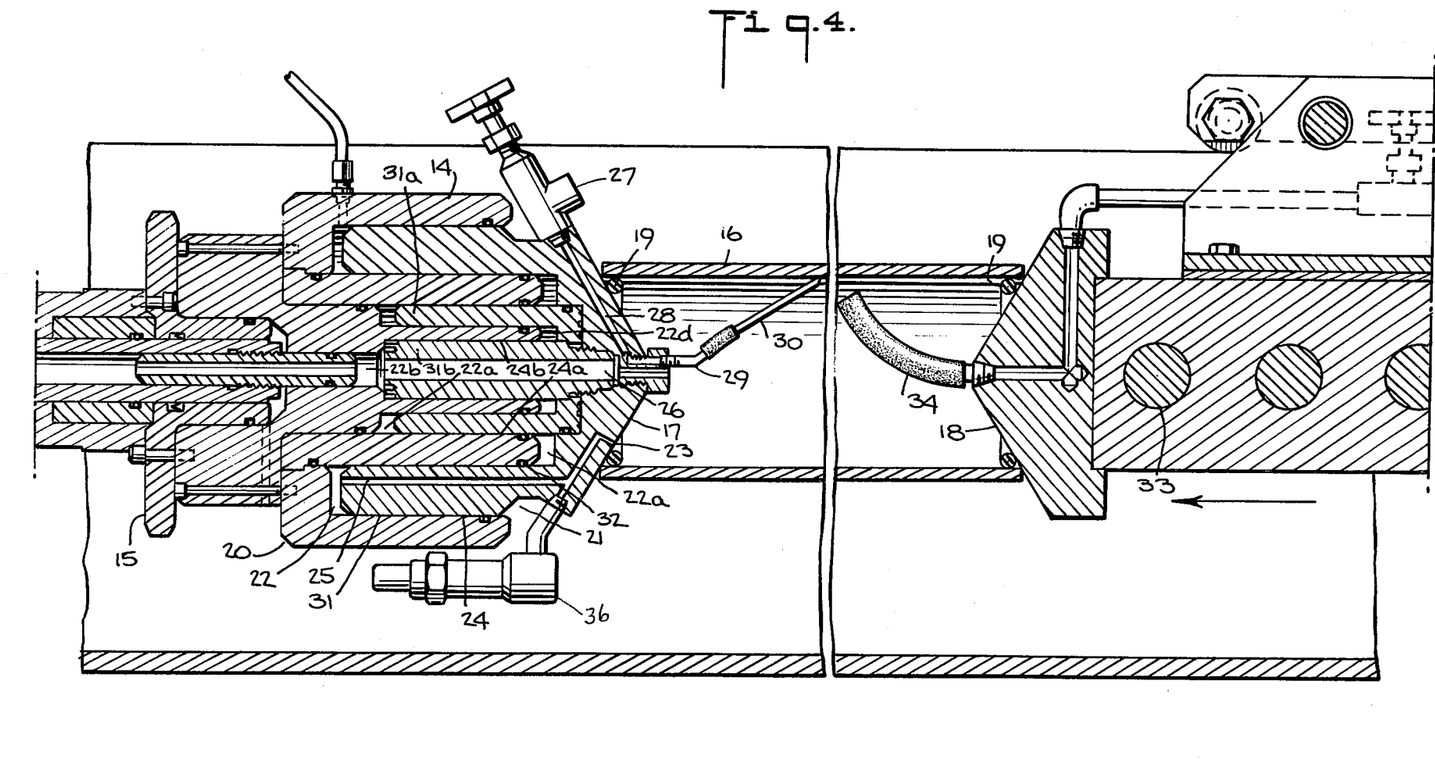
Figure 5:
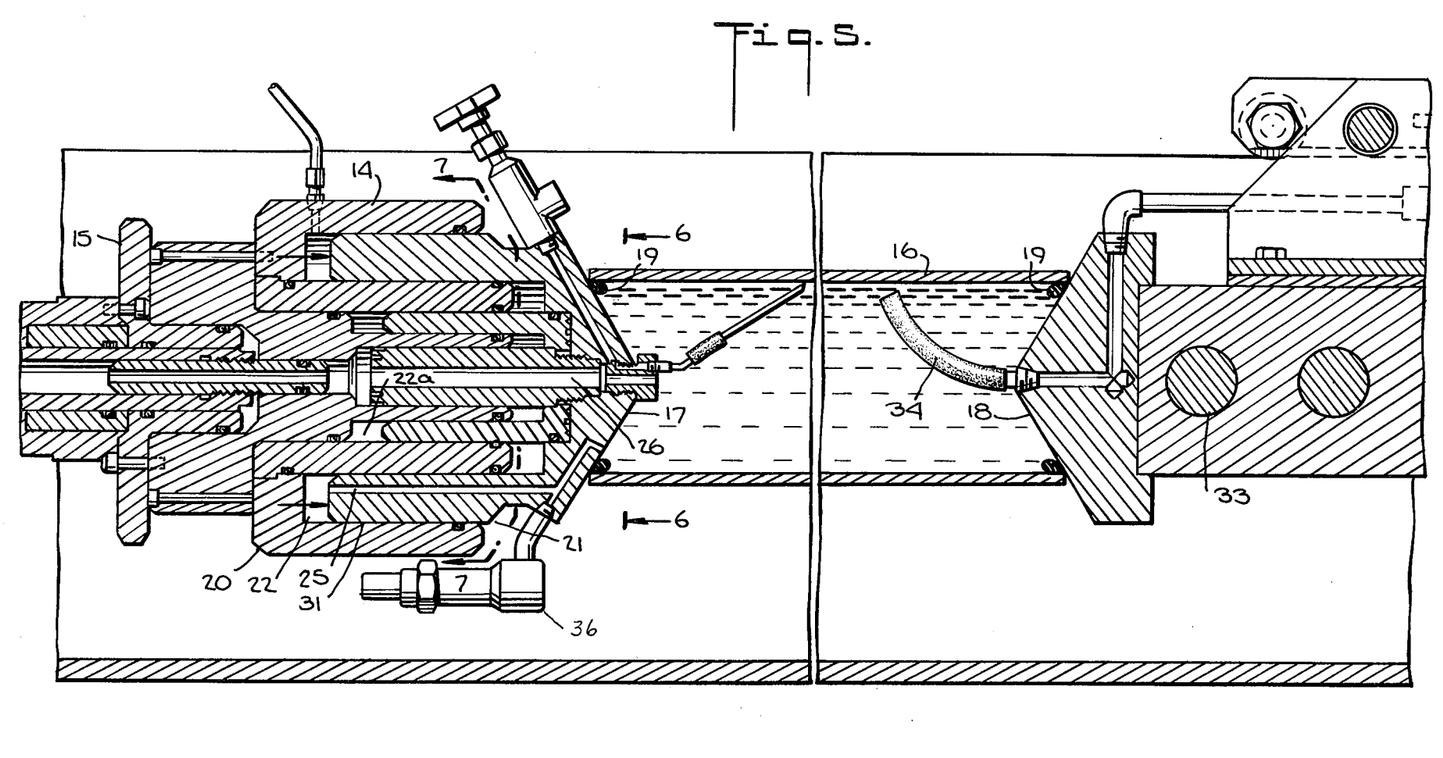

Turning now to the accompanying drawing, it will be seen that FIG. 1 represents a perspective view, partially in section, of apparatus in accordance with the invention. The apparatus comprises a frame indicated generally at 10 with rails 11 adapted for guiding the tailstock 12 by means of rollers 13. The headstock 14 is mounted at 15 on the frame. A tube, shown as 16 in FIGS. 4 and 5, is placed between the conical face 17 in the headstock and the conical face 18 in the tailstock and is firmly held between the conical faces. O-rings 19 are placed within the tube 16 at the junction between the tube ends and the headstock and tailstock conical faces so as to form seals therebetween under the action of hydraulic fluid within the tube 16. In operation, the tube is placed between the headstock face 17 and the tailstock face 18. The tailstock is run up the guide rails 11 to place the conical faces of the headstock and the tailstock within the ends of the tube 16. The tailstock is then locked in place on frame 10 by locking means indicated at 33 in FIGS. 4 and 5. The preplaced O-rings 19, which have a diameter equal to or slightly larger than the internal diameter of the tube, are then in contact with the conical faces and with the inside diameter of the tube to be tested so as to form a seal. Conveniently the conical faces have an included angle from the tailstock and headstock longitudinal axis of about 60°.

The placement of resilient O-rings 19 is shown in FIGS. 2 and 3 wherein location of the O-rings 19 prior to placement within the open ends of tube 16 is shown in FIG. 2 and location of resilient O-ring 19 within one end of tube 16 is shown in FIG. 3.

The action of internal fluid pressure within tube 16 in compressing the resilient O-ring into the junction formed between the wall of tube 16 and conical face 17 is shown more particularly in FIGS. 8 and 9 wherein FIG. 8 illustrates placement of O-ring 19 prior to start of the test and FIG. 9 illustrates the action of fluid pressure during the course of the test in forcing resilient O-ring into the junction of the tube wall and the conical face 17. FIGS. 8 and 9 illustrate clearly the importance of forming an acute angle between the conical face 18 and the wall of tube 16. The importance of forcing the conical faces toward each other with a pressure greater than the fluid pressure exerted by the tube ends against the conical faces 17 and 18 is also evident. It is to be appreciated that O-ring 19 at the tailstock face 18 undergoes similar compression during the course of the test.

Figure 7:
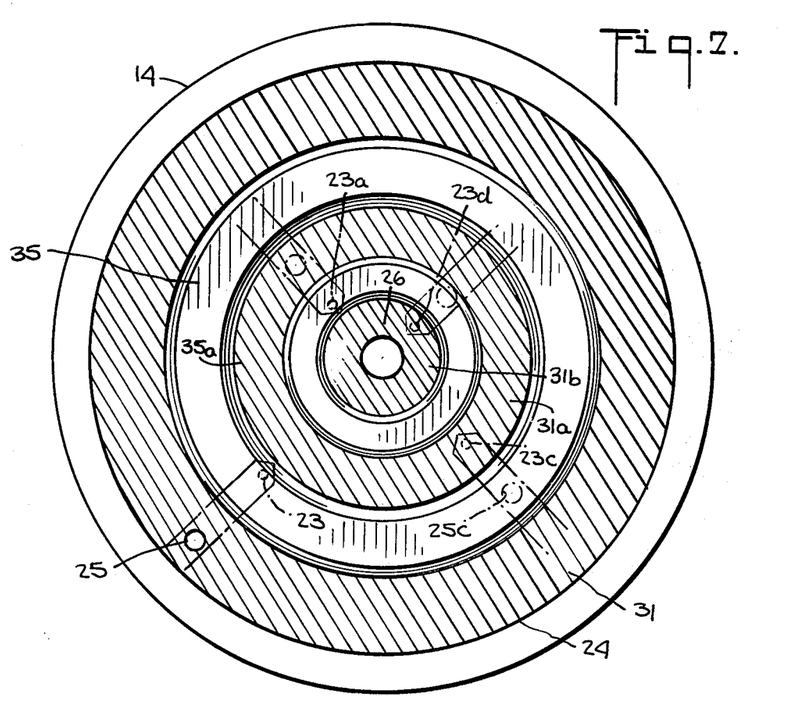
FIG. 7 is a section indicated at 7—7 in FIG. 5 depicting internal passages and hydraulic cylinders within the headstock shown in vertical section in FIGS. 4 and 5.
Figure 10:
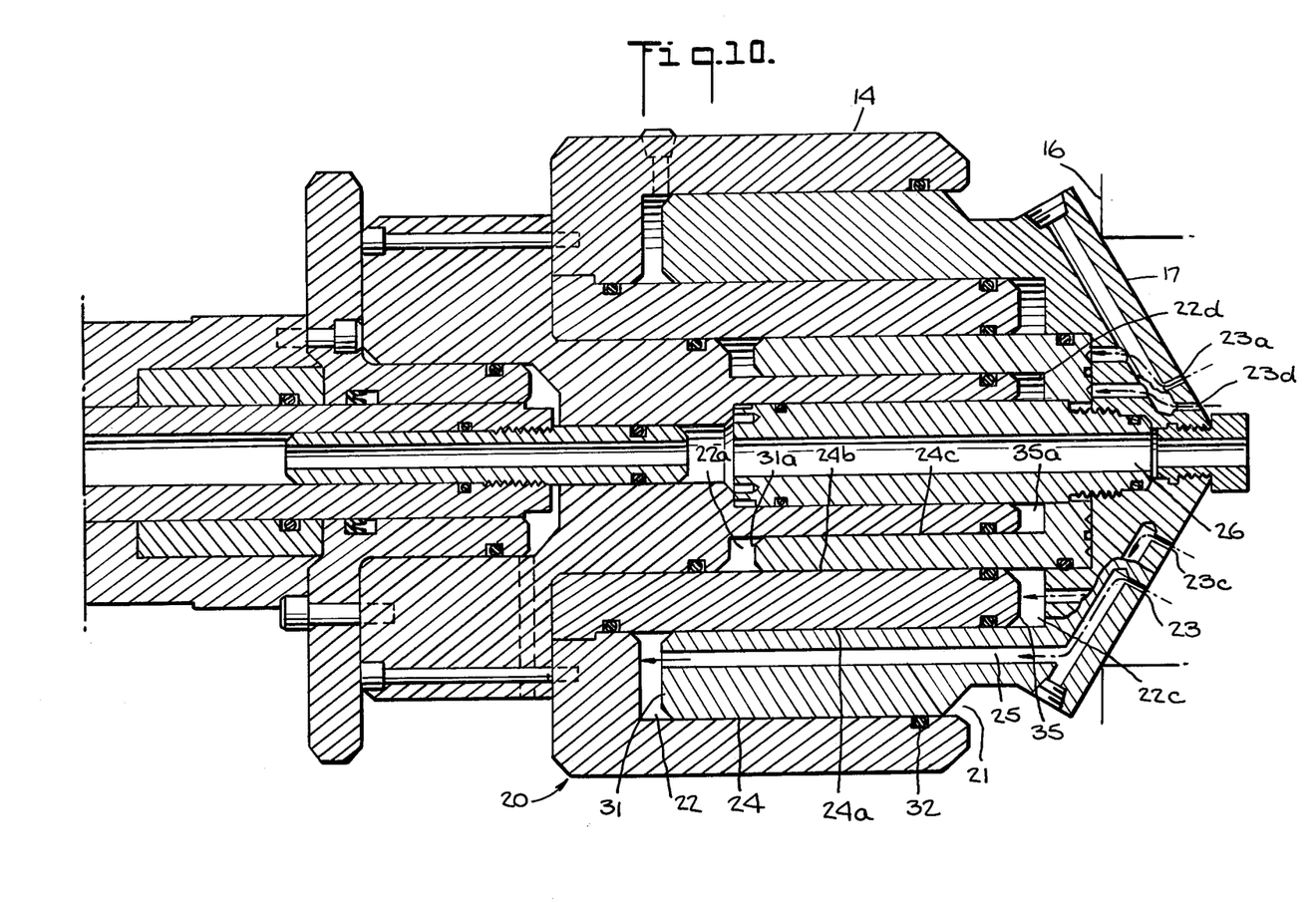
FIG. 10 is a vertical section of the headstock depicted in FIG. 1.

FIGS. 4 and 5, respectively, illustrate apparatus of the invention with tube 16 to be tested in place prior to hydraulic pressure testing and during hydraulic pressure testing. The forward element 21 of headstock 14 is shown slightly further advanced in FIG. 5 than in FIG. 4 due to hydraulic pressure communicated to the junction between the rearward portion or element 20 and the forward element 21 of headstock 14. In FIG. 10, wherein headstock 14 is depicted at an enlarged scale, sensing holes 23, 23a, 23b and 23c are shown communicating to cylinders 22, 22a, 22c and 22d through passages 25, 25a, 25c and 25d. The radial arrangement of cylinders as depicted permits application of hydraulic pressure over substantially the entire headstock area. FIG. 7 further depicts arrangement of the sensing holes on the headstock conical face 18.

Fluid pressure is created within the tube to be tested by inserting hydraulic fluid into the interior of the tube utilizing a passage within the headstock. The fluid pressure enters at least one sensing hole placed in the headstock face in the area within the inside diameter of the tube to be tested, which fluid pressure actuates a hydraulic cylinder within the headstock and thrusts the headstock face against the end of the tube so as to hold it firmly sealed during the test.

Turning now to FIGS. 4, 5 and 10 which depict the longitudinal, vertical section of headstock 14, it wll be seen that the headstock itself consists of two elements, a rearward element 20 mounted on the frame at 15 and a forward element 21 bearing the headstock conical face 17. As previously stated, the headstock elements 20 and 21 telescope together to form a series of annular hydraulic cylinders indicated generally by the FIGS. 22, 22a, 22b, 22c and 22d sensing holes in the conical face 17 communicate with each hydraulic cylinder. In FIGS. 4 and 5, sensing hole 23 is shown communicating with hydraulic cylinder 22 through passage 25. The headstock is provided with passage 26 for communication of the hydraulic testing fluid directly into the interior of the pipe to be tested. Bleed valve 27 may be employed for purpose of bleeding air from the interior of the tube when the test fluid is a liquid such as water. Passage 28 communicates to bleed valve 27 from the interior of the pipe being tested through nipple 29 and nipple extension 30. Nipple extension 30 may be made of elastomeric material and is designed to extend to the upper wall of the tube being tested so that most of the air can be bled off as testing liquid enters the tube.

It is to be seen that the structure depicted in FIGS. 4, 5 and 10 depict the hydraulic cylinders 22, 22a, 22c and 22d which actuate the face 17, which is illustrated as being conical for convenience, as being concentric annular cylinders as this construction is particularly convenient. The end areas of the cylinders may be variable. The elements 31 in the forward portion of the headstock, and the elements 35 in the rearward portion of the headstock have been depicted as annular pistons. Other mechanical constructions could be employed to provide forward hydraulic actuation of conical face 17 against the open end of the pipe 16 as long as the object is attained of providing sufficient area for action by the hydraulic fluid on the ends of the hydraulic pistons. Seals 32 are provided between the pistons 31, 31a, 31b and the cylinder walls 24, 24a, 24b and 24c so as to provide fluid tight faces between the pistons and the cylinder walls. It will be appreciated that bleed mechanisms may be provided in the tailstock as indicated at 34 in FIG. 4 as well as in the headstock and that bleed valve 27 may be employed to relieve hydraulic test pressure from the interior of the tube being tested once the pressure test is complete. Similar relief of hydraulic pressure through 34 in the tailstock can be provided.

It is to be appreciated that apparatus in accordance with the invention provides great flexibility in operation in that a wide variety of tube diameters and tube lengths can be tested in the same apparatus. It is only required that the faces on the headstock and tailstock which engage the ends of the pipe being tested be sufficiently large in diameter to fully cover the ends of the tube being subjected to hydraulic pressure. It is also to be appreciated that the hydraulic cylinders may take other configurations than that illustrated in FIG. 2.

Figure 6:
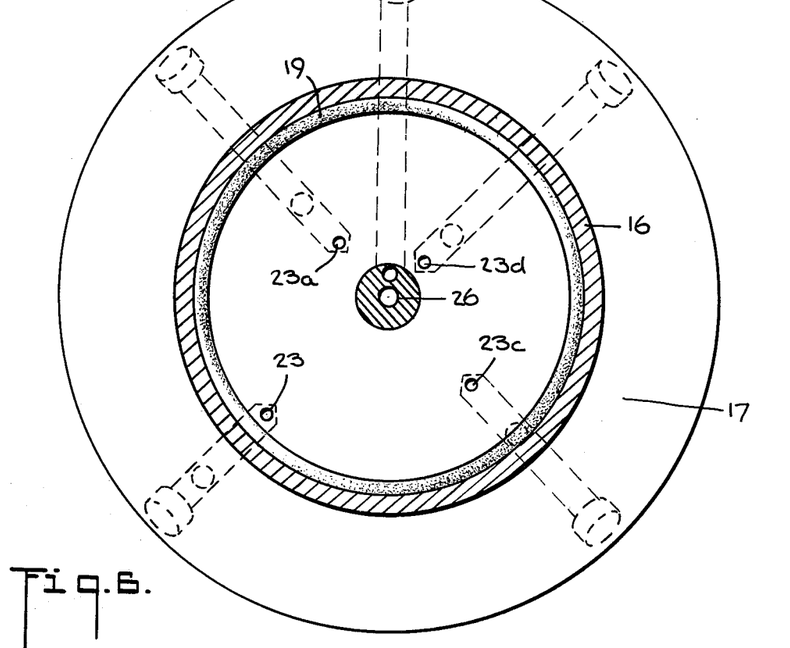
FIG. 6 is a section indicated at 6—6 in FIG. 5 depicting internal passages and external sensing holes in the face of the headstock shown in vertical section in FIGS. 4 and 5.

FIG. 6, taken at section 6—6 of FIG. 5 depicts the front view of the face of the movable portion of the headstock 14 and indicates location of the sensing holes 23 and fluid passage 26.

FIG. 7, taken at section 7—7 of FIG. 5 shows passage 25 communicating with the end of piston 31, passage 26 for communication of pressure test fluid to the interior of the tube being tested, and the annular sections of pistons 31, 31a and 31b. FIG. 7 demonstrates that practically the entire projected area of the junction between rearward and forward elements 20 and 21 of headstock 14 is available for application of fluid pressure on the ends of annular piston elements 31 and 35.

It will be appreciated, especially from FIG. 7, that spacing of the sensing holes 23 from the longitudinal centerline of headstock 14 can be at any convenient distance which can be a function of the pipe or tube diameters to be tested. It is only necessary that one sensing hole be located within the diameter of the pipe to be tested. Sensing holes falling beyond the inside diameter of the pipe to be tested are simply inactive since no supply of pressurized fluid would occur. It will also be appreciated that when the length:diameter ratio of the tube being tested is so high that column loading thereof during test would likely cause buckling appropriate supports or steady rests can be provided along frame 10. Wall thickness of the tube being tested is not a factor.

It is to be appreciated that in testing tubes of small inside diameter the central passage 26 can itself act as a sensing hole and the conical face 17 will be thrust forward by hydraulic pressure within 22b. It is further to be appreciated in connection with FIG. 8 that at the start of the test the resilient O-ring 19 need not be in contact with conical face 17 or 18. Close proximity to the conical face is sufficient since the action of the pressurized testing fluid will itself help to seat the O-ring in the junction between the tube end walls and the conical faces. In this connection the metal-to-metal contact of tube and face is not fluid tight. Also, as indicated at 36 in FIGS. 4 and 5, one or more over-pressure relief valves communicating with one or more of passages 25 may be provided to prevent distortion of frame 10.

In carrying out the method in accordance with the invention, a testing environment comprising opposing convex, preferably conical, faces having a common axis is provided. The conical faces are brought to bear against the ends of the tube to be tested wherein at each end a resilient O-ring has first been placed such that contact is made between the tube ends and the conical faces with the resilient O-ring. In this way, pressure within the tube to be tested forces the resilient O-ring into the junction between the conical faces and the tube ends and effectively seals the tube during test. The shape of the faces which contact the tube ends provides a self-centering feature and compensates for slight run-outs which may and frequently do occur in cutting off the tube in commercial cut-off operations. In this way, accurate machining of the ends of the tube is not required in order to effectively conduct a pressure test thereon. Once the conical faces and the O-rings are in place and hydraulic fluid under pressure is inserted within the tube body, the testing fluid is conducted to the hydraulic cylinder or cylinders within the headstock and hydraulic action against the ends of the hydraulic pistons thrusts the movable forward piece in the headstock against the end of the tube and maintains the conical face in position against the opposing thrust of hydraulic test pressure against the conical face. This is accomplished by providing sufficient area against which the hydraulic fluid may act during the course of the test in the hydraulic cylinder. The area of the hydraulic cylinder is always greater than the area of the interior diameter of the tube end to accomplish this result. Once the pressure test is complete, normally involving the application of up to about 10,000 psi of hydraulic pressure, e.g., hydraulic pressure in the range of 0 to about 10,000 psi gauge, the pump driving the hydraulic fluid is shut off and the pressure is released through the bleed valve or other convenient means provided for this purpose. The tube may then be removed merely by moving the tailstock away from the end of the tube and the next tube can be inserted in the apparatus for testing. Assembly of the tube in the apparatus is quick and easy to perform and no particular skill is required. Furthermore, excessive column-type loading on the tube or pipe while under test is avoided. Since the tubes or pipes to be tested will usually be metallic, i.e., steel, nickel-base alloy, nickel, copper, etc., it is convenient to make the convex or conical face elements from hardened steel, high-strength, age-hardenable nickel base alloys, etc., while the other required parts may be prepared from constructional grades of steel.

Although the present invention has been described in conjunction with preferred embodiments, it is to be understood that modifications and variations may be resorted to without departing from the spirit and scope of the invention, as those skilled in the art will readily understand. Such modifications and variations are considered to be within the purview and scope of the invention and appended claims.

We claim:

1. Apparatus for fluid pressure testing of tubular bodies having a range of diameters comprising a headstock, a tailstock, with each of said headstock and said tailstock having convex faces projecting toward each other along a common axis, and a plurality of O-ring seals having diameters corresponding to the inside diameters of the tubular bodies to be tested, said convex faces each being larger in base diameter than the internal diameter of any tubular body to be pressure tested and being adapted, in combination, to hold a tubular body therebetween and to form a pressure-tight seal therewith at the ends thereof by means of said resilient O-ring seals placed within said tubular body at each junction of said convex faces and the ends of said tubular body, said headstock comprising telescoping rearward and forward elements with said rearward element being fixably mounted and with said forward element bearing said convex face, said headstock convex face having at least one sensing hole communicating from a location within the internal diameter of a tubular body to be tested in place thereon through said forward telescoping element to the junction between said telescoping elements whereby fluid pressure communicating from said sensing hole to said junction acts hydraulically to urge said forward telescoping element away from said rearward telescoping element and against the end of said tubular element in contact with said convex face of said forward telescoping element during test to hold said O-ring seals closed against the opposing action of testing fluid within said tubular body.

2. Apparatus according to claim 1 comprising a frame holding said headstock, guiding means holding said tailstock in alignment with said headstock, means for moving said tailstock along said guiding means, and means for locking said tailstock to said frame.

3. Apparatus accordng to claim 2 wherein said convex faces are conical in configuration.

4. Apparatus according to claim 3 wherein the junction of said rearward and said forward elements of said headstock includes at least one annular hydraulic cylinder substantially concentric about the longitudinal axis of said elements and having an effective area exceeding the internal area of the tubular body to be tested.

5. Apparatus according to claim 4 wherein said headstock is provided with a passage for inserting pressurized testing fluid within a tubular body to be tested.

6. Apparatus according to claim 5 wherein said headstock is provided with fluid bleed means.

7. Apparatus according to claim 1 wherein said tailstock is provided with fluid bleed means.

8. Apparatus according to claim 1 wherein pressure relief means are provided.

9. Apparatus in accordance with claim 1 wherein the junction of said rearward and said forward elements of said headstock comprises a plurality of annular hydraulic piston and cylinder combinations with said pistons being alternately in said rearward and forward elements and with fluid pressure supply means communicating to the ends of each of said pistons from a respective one of said at least one sensing hole located in the face of said headstock.

10. In the method for hydraulic pressure testing open-ended tubular bodies wherein the ends of the bodies are sealed such that pressurized hydraulic fluid can be introduced into the interior of the body, the fluid pressure can be maintained at a desired level to permit inspection of the tubular body for resistance to internal pressure and the pressure can be relieved at the completion of the test, the improvement permitting fluid pressure testing of tubular bodies having a variety of diameters which comprises establishing a testing environment comprising opposing conical faces having a common longitudinal axis and a cone base diameter greater than that of any tubular body to be tested and with at least one of said conical faces being provided with at least one sensing hole located within the diameter of the tubular body to be tested and communicating to a hydraulic cylinder having a substantially greater effective area than the internal cross-sectional area of said tubular element, inserting resilient O-ring seals within each end of a tubular body to be tested adjacent the open ends thereof, closing the ends of said tubular body to be tested by inserting said conical faces therein in close juxtaposition to said resilient O-ring seals, inserting pressurized test fluid within the interior of said tubular body to be tested and maintaining said conical surfaces in position during the course of the test by hydraulic action of said testing fluid communicating to said hydraulic cylinder while said resilient O-rings are compressed firmly into the junctions between the ends of said tubular body undergoing test and said conical faces by said testing fluid.

* * * * *